United States Patent [19]

Dennis et al.

[11] Patent Number: 4,463,176
[45] Date of Patent: Jul. 31, 1984

[54] PROCESS FOR RESOLUTION OF OPTICAL ISOMERS

[75] Inventors: Ronald D. Dennis; Terence M. Dolak; William E. Kreighbaum, all of Evansville, Ind.

[73] Assignee: Mead Johnson & Company, Evansville, Ind.

[21] Appl. No.: 417,794

[22] Filed: Sep. 13, 1982

[51] Int. Cl.$^3$ .......................................... C07D 401/12
[52] U.S. Cl. .................................... 546/208; 546/141; 546/153; 546/193; 546/201; 546/202; 546/205; 546/210; 546/288; 548/465; 548/472; 548/135; 548/136; 548/523; 548/527; 548/525; 548/517; 548/541; 548/550; 548/478; 549/57; 549/63; 549/469; 549/480; 544/153; 544/147; 544/129; 544/124; 544/141; 544/128; 544/145; 544/144; 564/303; 544/146; 564/308; 544/134
[58] Field of Search ................ 564/303, 304; 546/288; 546/141, 153, 193, 201, 210, 202, 205, 208; 544/134, 144, 145, 146, 141, 128, 129, 124, 133, 147; 548/478, 465, 472, 135, 136, 523, 527, 525, 517, 541, 550; 549/57, 63, 467, 480

[56] References Cited

PUBLICATIONS

The Merck Index, Ninth Edition, p. 968, Merck and Co., Inc., Rahway, N.J., U.S.A. (1976).
USAN and the USP Dictionary of Drug Names (USPC, Inc.) Rockville, MD., U.S.A. (1982) p. 369.
Tsuru et al., Clinical Pharmacology and Therapeutics, pp. 275-276 (Feb. 1982) (Abstract E6).
Mead Johnson Pharmaceutical Division Pharmaceutical Research, Chemical Research Program Report No. 15.
O'Donnell et al. "Clin. Exp. Pharmacol.", vol. 8, No. 6, pp. 614-615 (1981).
Eckardt et al. "Die Pharmazie", vol. 30, pp. 633-637 (1975).
Jacques et al., "Enantiomers, Racemates and Resolutions", pp. 330-335 (Wiley) (1981).
Whitmore "Organic Chemistry", p. 551 (Van Nostrand) (1937).
Kolomiets et al. "Zh. Org. Khim. (English Ed.), vol. 16, No. 5, pp. 854-857 (1980).
Woodward "Pure Appl. Chem.", vol. 17, pp. 524-525 (1968).
Manske "J. Am. Chem. Soc.", vol. 51, p. 1202 (1929).
Houben-Weyl "Methoden der Organische Chemie" 4th Ed. Stickstoff-Verbindungen II 11/1 (1957), pp. 952-953.
Smith "The Chemistry of Open-Chain Nitrogen Compounds", vol. I (Benjamin) (1965) p. 270.
Barton et al. "Comprehensive Organic Chemistry", vol. II, Nitrogen Compounds, Carboxylic Acids, Phosphorus Compounds (Pergamon) (1979) p. 1095.

Primary Examiner—Robert T. Bond
Attorney, Agent, or Firm—Richard P. Ryan; Robert H. Uloth

[57] ABSTRACT

A process for resolving a racemic modification of β-adrenergic aryl- or hetaryl-oxypropanolamines such as (±)-2-[2-hydroxy-3-[[2-(1H-indol-3-yl)-1,1-dimethylethyl]amino]propoxy]benzonitrile into its individual enantiomers is described. The process comprises converting the racemic modification into a pair of diastereomeric urea derivatives by reaction with a chiral aralkylisocyanate; separation into the individual diastereomers; and facile regeneration of the starting amine by cleavage of the intermediate urea compound using hydrazine. This final step is improved by the addition of an α-keto carboxylic acid, such as pyruvic acid, which functions as a scavenger of nucleophilic by-products.

10 Claims, No Drawings

PROCESS FOR RESOLUTION OF OPTICAL ISOMERS

BACKGROUND OF THE INVENTION

It is well established that many β-adrenergic agents elicit more than a single biological effect following administration. Resolution of the optical isomers of these agents which contain asymmetric centers has, in many instances, demonstrated marked differences in potency between these isomers. In addition to increasing knowledge of receptor site topography, the pharmacologic profiles of the individual isomers may provide new and/or more desirable drug entities.

Previously, the optical isomers of β-adrenergic agents have most generally been obtained by one of three basic methods: (1) the fractional recrystallization of chiral acid salt derivatives; (2) synthesis of the single optical isomer using chiral epoxide intermediates; and, more recently, (3) column chromatography utilizing chiral stationary phases. The difficulties associated with application of these methods are well known to practitioners in the art, specifically, the tedious and time-consuming fractional recrystallizations and repeated chromatography; requisite chiral syntheses of epoxide intermediates with the attendant complications associated with stereospecific synthesis, and size limitation of quantities obtained via chromatography. Generally, preparation of a single enantiomer by these methods is quite expensive.

Another resolving method, derivatization with a chiral organic reagent, has been used for resolution of compounds which can form derivatives. β-Adrenergic agents in general have two functional moieties amenable to derivatization, i.e. secondary amino and alcohol functionalities. The resolution of amines and alcohols by derivatization with chiral acyl halides or isocyanates is well known in the chemical literature. The success of such a resolution strategy depends upon several factors, notably (1) formation of the diastereomeric derivatives in reasonably high yield, (2) facile separation of these diastereomers by chromatographic or crystallization techniques, and (3) the regeneration of the parent compound from the separated diastereomeric derivatives. To our knowledge, this technique has never been utilized for the resolution of β-adrenergic propanolamines.

The following references disclose β-adrenergic propanolamines having a urea moiety incorporated into their structure.

1. O'Donnell, et al, *Clin. Exp. Pharmacol.*, 8/6, 614–615 (1981) disclose a β-adrenergic agent (ICI 89963) with a urea moiety in the terminal alkyl portion of the structure.

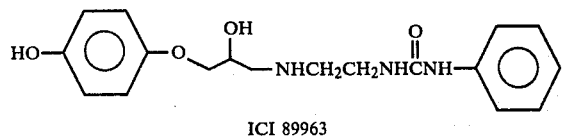

ICI 89963

2. Eckardt, et al., *Die Pharmazie*, 30, 633–637 (1975) disclose β-blocking propanolamines with urea substituents on the aryl portion of the molecule:

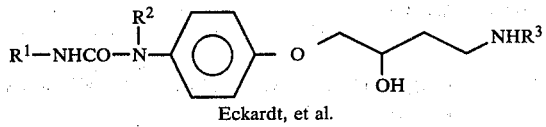

Eckardt, et al.

These urea compounds differ structurally from the urea intermediates of the instant process as the propanolamine nitrogen of the reference compounds is not a component of the urea grouping.

The next grouping of references relate to methods of resolution of optical isomers which are deemed most relevant to the instant process described herein.

3. J. Jacques, A. Collet, S. H. Wilen, in "Enantiomers, Racemates, and Resolutions", John Wiley & Sons, New York, N.Y. (1981), pp. 330–335. This reference describes, among other things, formation and separation of diastereomers comprising covalent derivatives of amines and alcohols. Specifically, amines may be resolved through conversion into diastereomeric ureas by reaction with optically active isocyanates; and, following separation of the diastereomeric ureas by crystallization or by chromatography, the resolved amine is recovered through pyrrolysis.

4. F. C. Whitmore in "Organic Chemistry", D. Van Nostrand Co., New York, N.Y. (1937), p. 551. This reference reports that dl-β-amino-lactic aldehyde dimethyl acetal, $H_2NCH_2CHOHCH(OMe)_2$, gave diastereomeric ureas when treated with l-menthyl isocyanate, as part of a scheme to prepare optically active glyceraldehydes.

5. Kolomoietes, et al. Zh. Org. Khim., English Edition, 16/5, pp. 854–857 (1980). This reference describes kinetic resolution of secondary alcohols and amines using S-(−)-α-phenylethylisocyanate.

It is appreciated by the practitioner in the art, that derivatization of β-adrenergic aryloxypropanolamines might be expected to present difficulties by virtue of the molecule containing two reactive functionalities, e.g. both an amine and an alcohol moiety.

Reference 4., supra, is the only example of which we are aware that reports diastereomeric urea derivatization by isocyanate treatment of a molecule containing both amino and hydroxy moieties. The compound being derivatized in the work mentioned by Whitmore is not related to the β-adrenergic propanolamine structure. The terminal primary amino group as opposed to the secondary hydroxyl in $H_2NCH_2CHOH(OMe)_2$ would be expected to be more accessible sterically to electrophilic attack by an isocyanate. Any steric advantage of the amino group is negated in β-adrenergic structures in which the amino nitrogen is further substituted with an alkyl group, which is usually branched, thereby giving a more hindered secondary amine. It would reasonably be expected prior to the instant invention that reaction of an optically active isocyanate and a β-adrenergic aryloxypropanolamine would result in a complex product mixture containing both diastereomeric ureas and carbamates. In practice, it is discovered that the reaction takes place preferentially at the site of the amine moiety, even when sterically hindered, giving predominently as novel intermediates the diastereomeric urea derivatives. This reaction selectivity forms the basis for the first step of the instant process.

The other major complication accompanying derivative resolution is the regeneration of the parent compound from the separated diastereomeric derivative. It is appreciated that ureas as a class of compounds are inherently stable and generally require more stringent methods, e.g. pyrrolysis or strong hydrolyzing conditions, for their decomposition. Since many of the β-adrenergic aryloxypropanolamines, especially those with sensitive substituents, would be labile under these same conditions, the regeneration step of the instant process becomes quite important.

The following references relate to methods of cleaving ureas in order to produce a parent amine.

6. Woodward, *Pure Appl. Chem.*, 17 (1968), pp. 524–525. Woodward discloses the resolution of a racemic amine mixture by forming diastereomeric ureas with optically active α-phenylethyl isocyanate. Following separation of the diastereomers, the optically active amine is generated by pyrrolysis of the urea.

7. (a) Manske, *J. American Chemical Society*, 51, (1929) p. 1202. (b) Houben-Weyl "Methoden der Organische Chemie". Vierte Auflage Stickstoff-Verbindungen II, 11/1 (1957), pp. 952–953. (c) P. A. S. Smith, "The Chemistry of Open-Chain Organic Nitrogen Compounds" Volume I, W. A. Benjamin, Inc., New York, N.Y. (1965), p 270. (d) D. Barton and W. D. Ollis, in "Comprehensive Organic Chemistry" Volume II, Nitrogen Compounds, Carboxylic Acids, Phosphorus Compounds, Pergamon Press, Ltd. (1979), p. 1095. These four references are representative of the chemical literature which teaches that hydrolysis of urea compounds is not easy and usually requires prolonged heating with strong mineral acid or alkali.

A convenient mild reaction for breakdown of the useful intermediate urea derivatives, thereby regenerating the desired amine in optically active form, has been developed as part of the instant process.

SUMMARY OF THE INVENTION

This invention describes an improved, convenient process for resolution of optical isomers of selected aryl- or hetaryloxypropanolamines of Formula I, a structural class of β-adrenergic agents. The process is amenable for large-scale manufacture.

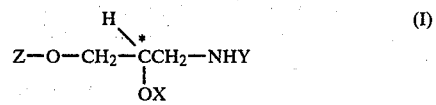

For compounds of Formula I: Z is substituted or unsubstituted aryl or hetaryl; Y is alkyl, aralkyl, or hetarylalkyl; and X is hydrogen or acyl.

This process comprises treatment of the racemic mixture of β-adrenergic propanolamines with a chiral isocyanate to give novel diastereomeric urea intermediates; separation of these into the individual diastereomers; and facile regeneration of each optical isomer of the starting amine by cleavage of the intermediate urea compound with hydrazine. Use of an α-keto carboxylic acid, such as pyruvic acid, in the regeneration reaction allows for improved isolation and purification of the optical isomers.

DETAILED DESCRIPTION OF THE INVENTION

β-Adrenergic aryl- or hetaryl-oxypropanol amines, resolved by the instant process, are characterized by structural formula I.

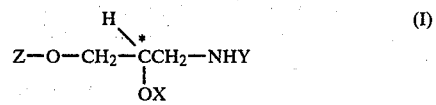

Z in formula I represents a substituted or unsubstituted aryl group such as phenyl, tetralyl, indanyl, indenyl, and naphthyl; or a hetaryl group such as pyridine, benzopyridine, pyrrole, benzopyrrole, furan, benzofuran, thiophene, benzothiophene, pyrimidine, or thiadiazole.

These aryl or hetaryl systems can be substituted by one or more of the following groups comprising lower ($C_1$–$C_6$) alkyl, lower alkoxy, lower alkenyl, lower alkenyloxy, lower alkynyl, lower alkynyloxy, lower alkoxy-lower alkyl, lower alkoxy-lower alkoxy, lower alkylthio, lower alkenylthio, lower alkylthio-lower alkyl, lower alkoxy-lower alkylthio, halogen, halogen-lower alkyl, hydroxyl, hydroxyl-lower alkyl, carboxyl, carbamoyl, N-lower alkyl carbamoyl, N,N-dilower alkyl carbamoyl, N-lower alkyl carbamoyl-lower alkyl, N,N-di-lower alkyl carbamoyl-lower alkyl, lower alkanoylamino-lower alkenyl, N-lower alkylamino, N,N-di-lower alkylamino, lower alkoxycarbonyl, lower alkoxy-carbonylamino, lower alkoxy-carbonylamino-lower alkyl, lower alkoxycarbonylamino-lower alkenyl, lower alkoxycarbonylamino-lower alkoxy, lower alkylcarbonylamino-lower alkyl, N'-lower alkyl-ureido, N,N'-di-lower alkyl-ureido, lower alkylsulfonylamino, cyano, nitro, lower alkanoyl, lower alkenoyl, lower cycloalkyl, lower cycloalkenyl, carbamoyl-lower alkyl, lower alkyl carbamoyl-lower alkoxy, lower alkyl-lower alkoxy, N-morpholino, hydroxy, and halogen. It is preferred that Z have ortho-substitution.

Y in Formula I is either $C_1$ to $C_{10}$ alkyl or AB wherein A is an alkyl chain from 1 to 10 carbons, branched and unbranched, and B is a substituted or unsubstituted aryl group, preferably phenyl, or hetaryl group such as pyridine, benzopyridine, pyrrole, benzopyrrole, furan, benzofuran, thiophene, benzothiophene, pyrrolidine, or piperidine. Substituent groups attached to A comprise lower alkyl, alkoxy, alkenyl, nitro, hydroxy, amino, cyano, or halogen.

X is hydrogen or

wherein R is $C_1$ to $C_{10}$ alkyl, substituted or unsubstituted phenyl, or alkylphenyl.

The substituent groups of the radicals Z and Y, listed above, may be more specifically defined. The term lower alkyl as used hereinabove denotes cyclic, straight and branched chain alkyl groups of 1–6 carbon atoms inclusive, such as methyl, ethyl, n-propyl, isopropyl, n-butyl, isobutyl, tert.-butyl, pentyl, or cyclohexyl radicals bonded in any desired position.

The term lower alkenyl denotes straight and branched chain alkenyl groups of 2–6 carbon atoms, especially allyl or methallyl radicals.

The term lower alkynyl includes the straight or branched chain alkynyl groups of 2–6 carbons, with the propargyl radical being especially suited.

The term lower alkyloxy or lower alkoxy denotes straight or branched chain alkoxy groups of 1–6 carbon atoms, for example, methoxy, ethoxy, propoxy, butoxy, and the like.

The term lower alkenyloxy denotes straight and branched chain lower alkenyloxy groups and the positional isomers thereof, having 2–6 carbons, for example, ethenoxy, propenoxy, butenoxy, and the like.

The term lower alkynyloxy embraces straight and branched chain alkynyloxy groups of 2–6 carbon atoms, such as ethynyloxy, 2-propynyloxy, 3-butynyloxy, and the like.

The term lower alkoxy-lower alkyl embraces methoxymethyl, ethoxymethyl, isopropoxyethyl, and the like. The term lower alkoxy-lower alkoxy embraces for example methoxymethoxy, methoxyethoxy, ethoxyethoxy, ethoxyisopropoxy, and the like. The term hydroxy-lower alkyl is, for example, hydroxymethyl, 1- or 2-hydroxyethyl and the like.

The term lower alkylthio is, for example, methylthio, ethylthio, isopropylthio, n-butylthio, and the like. The term lower alkenylthio is illustrated by 1-propenylthio, 1-butenylthio, 3-pentenylthio, and the like. Lower alkylthio-lower alkyl is illustrated by methylthiomethyl, methylthioethyl, 2-ethylthioethyl, and the like. Lower alkoxy-lower alkylthio is illustrated by methoxymethylthio, ethoxymethylthio, and the like.

The term halogen is depicted by fluorine, chlorine, bromine, and iodine, especially fluorine or chlorine. The term halogen-lower alkyl is exemplified by trifluoromethyl, trichloromethyl, and the like.

It should also be understood that certain substituents as the group set forth hereinabove may be attached to the Z ring at two sites, usually adjoining ring atoms, to give, for example: tetralins, tetralones, indanes, indanones, indenes, and the like.

Adrenergic propanolamines embraced by structure I for the purpose of this invention are exemplified by the following beneficial drugs which contain centers of asymmetry. Exemplary drugs are acebutolol or N-[3-acetyl-4-[2-hydroxy-3-[(1-methylethyl)amino]propoxy]phenyl]butanamide; alprenolol or 1-[(1-methylethyl)amino]-3-[2-(2-propenyl)-phenoxy]-2-propanol; atenolol or 1-p-carbamoylmethylphenoxy-3-isopropylamino-2-propanol; bevantolol or 1-[(3,4-dimethoxyphenethyl)amino]-3-(m-tolyloxy)-2-propanol; buprenolol or 1-(tert.-butylamino)-3-[(6-chloro-m-tolyl)oxy]-2-propanol; bunitrolol or 2-[3-[1,1-dimethylethyl)amino]-2-hydroxypropoxy]benzonitrile; bunolol or 5-[3-[(1,1-dimethylethyl)amino]-2-hydroxypropoxy]-3,4-dihydro-1(2H)-naphthalenone; exaprolol or 1-(o-cyclohexylphenoxy)-3-(isopropylamino)-2-propanol; indanolol or 1-[indan-4-yloxy]-3-[1-methylethylamino]-2-propanol; metoprolol or 1-(isopropylamino)-3-[p-(2-methoxyethyl)phenoxy]-2-propanol; moprolol or 1-(2-methoxyphenoxy)-3-[(1-methylethyl)amino]-2-propanol; oxprenolol or 1-(isopropylamino)-2-hydroxy-3-[o-(allyloxy)phenoxy]propane; pamatolol or methyl-[p-[2-hydroxy-3-(isopropylamino)propoxy]phenethyl]carbamate; penbutolol or 1-(2-cyclopentylphenoxy)-3-[(1,1-dimethylethyl)amino]-2-propanol; pargolol or 1-(tert.-butylamino)-3-[o-(2-propynyloxy)phenoxy]-2-propanol; procinolol or 1-(o-cyclopropylphenoxy)-3-(isopropylamino)-2-propanol; practolol or 1-(4-acetamidophenoxy)-3-isopropylamino-2-propanol; tiprenolol or 1-[(1-methylethyl)amino]-3-[2-(methylthio)phenoxy]-2-propanol; tolamolol or 4-[2-[[2-hydroxy-3-(2-methylphenoxy)propyl]amino]ethoxy]benzamide; toliprolol or 1-(isopropylamino)-3-(m-tolyloxy)-2-propanol; nadolol or 1-(tert.-butylamino)-3-[(5,6,7,8-tetrahydro-cis-6,7-dihydroxy-1-naphthyl)oxy]-2-propanol; pindolol or 1-(indol-4-yloxy)-3-(isopropylamino)-2-propanol; and timolol or 1-(tert.-butylamino)-3-[(4-morpholino-1,2,5-thiadiazol-3-yl)oxy]-2-propanol. These beta-adrenergic propanolamines are known to the art, appearing in the Merck Index, Unlisted Drugs, USAN and USP Dictionary of Drug Names, and Annual Reports in Medicinal Chemistry, Vol. 10, pages 51–60 (1975), and ibid., Vol. 14, pages 81–90 (1979).

Certain conventions are used by those skilled in the art to designate optical rotation and spatial configuration of optical isomers. Individual enantiomers are commonly designated according to the optical rotation they effect, by (+) and (−), (l) and (d), or combinations of these symbols. The symbols (L) and (D) and the symbols (S) and (R), which stand for sinister and rectus, respectively, designate an absolute spatial configuration of the enantiomer. A complete resolution utilizing the instant process is detailed in the following section entitled Description of Specific Embodiments. Assignment of absolute configuration to the enantiomers separated therein is tentative and is based on the usual assignment of S-configuration to the β-adrenergic aryloxypropanolamine enantiomer with negative rotation.

The following flow chart, Scheme 1, illustrates the resolution of a racemic mixture of β-adrenergic propanolamines utilizing the instant process.

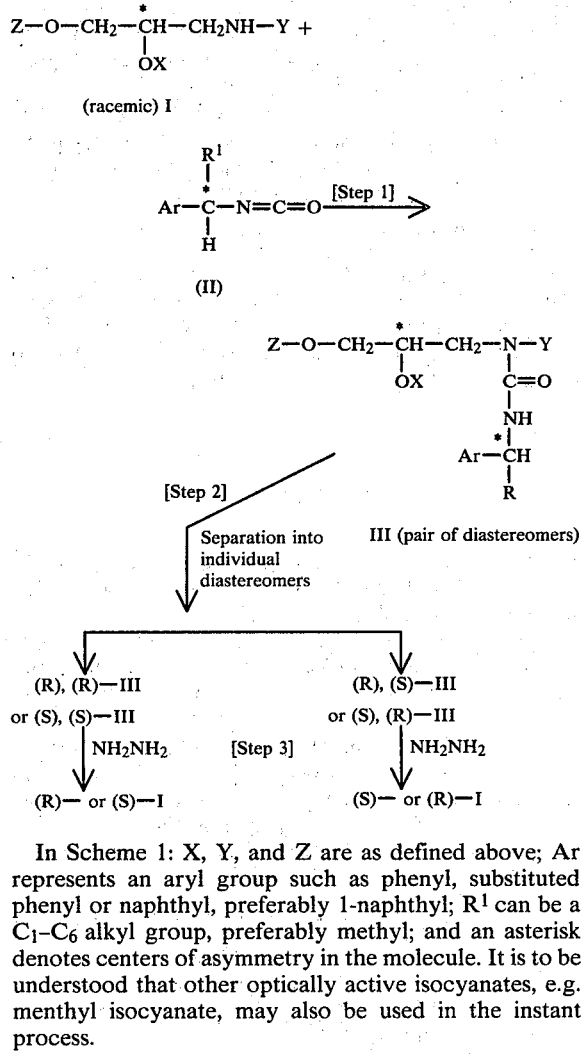

In Scheme 1: X, Y, and Z are as defined above; Ar represents an aryl group such as phenyl, substituted phenyl or naphthyl, preferably 1-naphthyl; $R^1$ can be a $C_1$–$C_6$ alkyl group, preferably methyl; and an asterisk denotes centers of asymmetry in the molecule. It is to be understood that other optically active isocyanates, e.g. menthyl isocyanate, may also be used in the instant process.

Step 1 of the Scheme outlined above involves the reaction of the adrenergic propanolamine with a chiral isocyanate of structure II to give a pair of novel diastereomeric ureas of Formula III. The reaction of step 1 is accomplished simply by stirring together equimolar quantities of the adrenergic amine, in its free base form, and the chiral isocyanate in an inert organic liquid medium for several hours at approximately 25° C. The temperature can range from ambient room temperature up to the reflux temperature of the particular organic liquid used as reaction medium. This reaction is usually complete within four to eight hours. Suitable reaction liquids include but are not limited to benzene, tetrahydrofuran, dibutylether, dimethoxyethane, etc. A preferred reaction liquid is benzene.

In many instances, choice of an appropriate reaction liquid affects separation of the diastereomeric ureas by virtue of one of the diastereomers being soluble in the liquid and the other being insoluble. In other instances, where separation is not so easily accomplished, the physical separation, designated in Scheme 1 as Step 2, is accomplished by fractional recrystallization or chromotography. Separation of diastereomeric pairs using standard methodology is familiar to those skilled in the art.

Following separation into individual diastereomeric ureas, the enantiomeric adrenergic amine is regenerated in step 3 by refluxing one equivalent of the urea compound (III) with excess 85–99% hydrazine hydrate in ethanol. The amount of excess hydrazine may range from 2 to 20 equivalents with 5 equivalents preferred. This reaction is usually complete in one hour or less. Isolation and purification of the amine enantiomer is greatly facilitated by use of a nucleophile-scavenger such as an $\alpha$-keto carboxylic acid; preferably an $\alpha$-keto alkanoic acid of 3 to 10 carbon atoms and most preferably pyruvic acid. Usually the $\alpha$-keto carboxylic acid is employed in an excess amount equal to the equivalents of hydrazine used. Following binding of the excess hydrazine-type nucleophilic species with the $\alpha$-keto acid, the resulting adduct is easily removed by treatment with base during aqueous washing of the reaction products dissolved in an organic phase.

The subject process, as mentioned, is particularly adaptable to large-scale resolution and in that respect is both economical and convenient. The entire process is carried out as a series of three steps going from the $\beta$-adrenergic amine in the form of a racemic mixture via diastereomeric ureas and regeneration into the optically pure isomers. The steps comprising the process are as follows:

(1) treating an appropriate $\beta$-adrenergic aryl- or hetaryl-oxypropanolamine, in the form of a racemic mixture, with a chiral isocyanate such as resolved 1-(1-naphthyl) ethyl isocyanate, by stirring for six to 12 hours in an inert organic liquid medium such as benzene at a temperature ranging from ambient room temperature up to the reflux temperature of the organic liquid, thereby giving a pair of diastereomeric ureas (III);

(2) separation of the diastereomeric pair into individual diastereomers using standard physical separation techniques well known to those skilled in the pertinent art; and (3) reacting the respective diastereomer of the urea derivative at reflux for approximately one hour or less in alcohol, preferably ethanol, with excess 85–99% hydrazine hydrate following which, the ethanol solvent is removed and the residue is dissolved in acetonitrile and an excess of an $\alpha$-keto carboxylic acid such as pyruvic acid is added and this mixture stirred at room temperature for eight to 12 hours.

Workup of the reaction mixture from step 3, including an acid-base extraction purification affords the respective amine enantiomer corresponding to the respective diastereomeric urea derivative employed.

DESCRIPTION OF SPECIFIC EMBODIMENTS

The process of this invention is further illustrated by the following examples directed to one of the preferred embodiments but these examples should not be construed as limiting the scope of the present invention. Melting points were determined using a Thomas-Hoover capillary melting point apparatus and are uncorrected. All temperatures are expressed in degrees Celsius. Optical rotation measurements were obtained on a Bendix-NPL 1169 automatic polarimeter with digital readout. The (R)-(−)-(1-naphthyl) ethyl isocyanate can be prepared as reported in the literature (Pirkle, et al, *J. Org. Chem.*, 39 (1974) pages 3904–3906) or is available commercially (Aldrich Chemical Company).

Scheme 2 illustrates a specific embodiment of this process as applied to bucindolol (IA) which is a novel antihypertensive agent currently under clinical investigation.

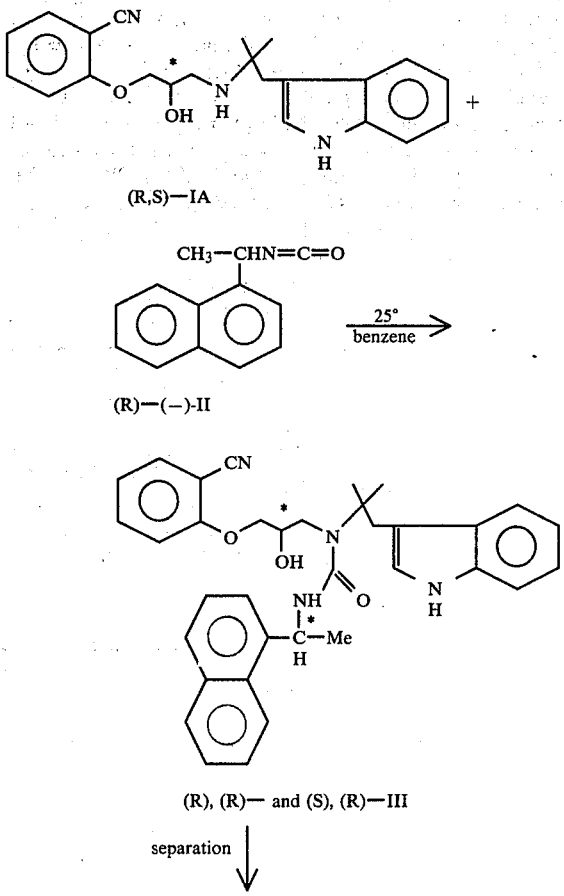

-continued
Scheme 2

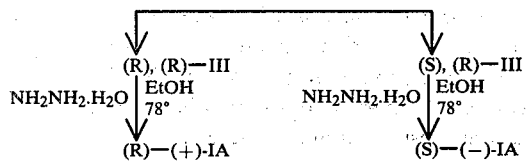

In examples which follow, the nuclear magnetic resonance (NMR) spectral characteristics refer to chemical shifts (δ) expressed as parts per million (ppm) versus tetramethylsilane (TMS) as reference standard. The relative area reported for the various shifts in the $^2$H NMR spectral data corresponds to the number of hydrogen atoms of a particular functional type in the molecule. The nature of the shifts as to multiplicity is reported as broad singlet (bs), singlet (s), multiplet (m), or doublet (d). Abbreviations employed are DMSO-d$_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

EXAMPLE 1

Diastereomeric Urea Derivatives of Bucindolol

A hot solution of bucindolol hydrochloride salt (100 g, 0.28 mole) and 2.5 L of H$_2$O was made basic with a 10% solution of NaOH. Bucindolol is 2-[2-hydroxy-3-[[2-(1H-indol-3-yl)-1,1-dimethylethyl]amino]propoxy]-benzonitrile; cf: Kreighbaum, et al, U.S. Pat. No. 4,234,595 patented Nov. 18, 1980, and *Journal of Medicinal Chemistry*, 23:3, 285-289 (1980). After being allowed to cool, the aqueous layer of the basic mixture was decanted and the residual gum rinsed with H$_2$O and crystallized from isopropyl alcohol (500 mL) to provide 81 g of bucindolol free base, m.p. 126°-128° C. The aqueous layer was allowed to stand overnight at 15° C., and a precipitate was collected by filtration, washed with H$_2$O, and dried in air overnight to give a further 3.5 g of bucindolol free base. This material, a mixture of (R,S)-bucindolol base, was then derivatized.

A mixture of (R,S)-bucindolol base (1.8 g, 0.005 mole), (R)-(−)-1-(1-naphthyl)-ethylisocyanate (1.0 g, 0.005 mole), and benzene (100 mL) was stirred at 25° for 6 hrs. A white solid was removed by filtration and dried in air to give 1.24 g of (S), (R)-N-[3-(2-cyanophenoxy)-2-hydroxypropyl]-N-[1,1-dimethyl-2-(1H-indol-3-yl)ethyl]-N'-[1-(1-naphthyl)ethyl]urea. This urea derivative melted at 167°-168° C. and gave a single spot on TLC (silica gel; CH$_2$Cl$_2$—EtOAc, 9:1) and rotation of $[\alpha]_D^{25}$ −14° (C 0.5%, CH$_3$OH).

Anal. Calcd. for C$_{35}$H$_{36}$N$_4$O$_3$: C, 74.98; H, 6.48; N, 10.00. Found: C, 74.89; H, 6.46; N, 9.74.

NMR (DMSO-d$_6$): 1.38 (6,s); 1.52 (3,d [6.7 Hz]); 3.35 (4,m); 3.94 (3,m); 5.70 (1,m); 6.23 (1,bs); 7.01 (5,m); 7.59 (11,m); 8.27 (1,d [9.5 Hz]); 10.72 (1,bs).

IR (KBr): 745, 1110, 1260, 1490, 1530, 1600, 1630, 2230, 2930, 2970, 3050, 3350, and 3410 cm$^{-1}$.

The benzene filtrate from above was concentrated to dryness and the residual material chromatographed on silica gel eluting with CH$_2$Cl$_2$—EtOAc (9:1) to give 0.70 g of (R), (R)-N-[3-(2-cyanophenoxy)-2-hydroxypropyl]-N-[1,1-dimethyl-2-(1H-indol-3-yl)ethyl]-N'-[1-(1-naphthyl)ethyl]urea as a foam. This material which did not crystallize had a rotation of $[\alpha]_D^{25}$ −119° (C 0.5%, CH$_3$OH).

Anal. Calcd. for C$_{35}$H$_{36}$N$_4$O$_3$·½EtOAc: C, 73.49; H, 6.67; N, 9.27. Found: C, 73.29; H, 6.60; N, 9.18.

NMR (DMSO-d$_6$): 1.36 (3,s); 1.52 (6,m); 3.36 (4,m); 3.92 (3,m); 5.76 (1,m); 6.30 (1,bs); 7.00 (5,m); 7.55 (11,m); 8.26 (1,d [9.0 Hz]); 10.78 (1,bs).

IR (KBr): 745, 1115, 1260, 1495, 1540, 1600, 1635, 2220, 2930, 2980, 3060, 3350, and 3420 cm$^{-1}$.

Treating racemic mixtures of other Formula I adrenergic amines with chiral isocyanates (II) using reaction procedures similar to those outlined above gives diastereomeric urea intermediates. Some additional examples of these are listed in Table 1.

TABLE 1

Adrenergic Propanolamine Urea Derivatives

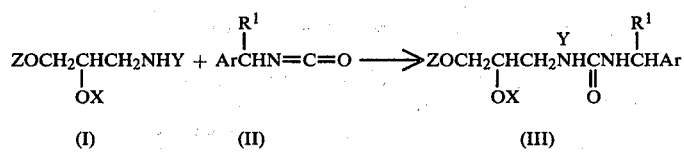

| | I | | | II | |
|---|---|---|---|---|---|
| Example | X | Y | Z | R | Ar |
| 2 | H | 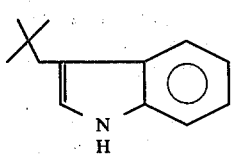 | 2-cyanopyridyl | Me | phenyl |
| 3 | H | i-Pr | 2-(2-propenyl)phenyl | Me | 1-naphthyl |
| 4 | H | i-Pr | 1-naphthyl | Me | 1-naphthyl |

TABLE 1-continued
Adrenergic Propanolamine Urea Derivatives $$\underset{(I)}{\text{ZOCH}_2\overset{\overset{R^1}{|}}{\text{CH}}\text{CH}_2\text{NHY}} + \underset{(II)}{\text{ArCHN}=\text{C}=\text{O}} \longrightarrow \underset{(III)}{\text{ZOCH}_2\overset{\overset{R^1}{|}}{\text{CH}}\text{CH}_2\overset{\overset{Y}{|}}{\text{N}}\overset{\|}{\underset{O}{\text{C}}}\text{NH}\overset{\overset{R^1}{|}}{\text{CH}}\text{Ar}}$$

| | I | | | II | |
|---|---|---|---|---|---|
| Example | X | Y | Z | R | Ar |
| 5 | H | t-Bu | (decahydronaphthalenyl =O structure) | Me | phenyl |
| 6 | H | i-Pr | 2-(2-propenyloxy)-phenyl | Me | phenyl |
| 7 | H | i-Pr | 4-(1H—inodolyl) | Et | phenyl |
| 8 | H | i-Pr | 4-acetanilide | Me | 1-naphthyl |
| 9 | H | i-Pr | 2-(methylthio)phenyl | Me | 1-naphthyl |
| 10 | H | i-Pr | 2-cyanopyridyl | Et | 1-naphthyl |
| 11 | H | t-Bu | 2-cyanopyridyl | Me | 4-nitrophenyl |
| 12 | acetyl | 2-(benzothiophen-3-yl)-1,1-dimethyl ethyl | 2-cyanopyridyl | Me | 1-naphthyl |
| 13 | H | 2-(1H—indol-3-yl-1,1-dimethylethyl | 2-cyanopyridyl | Me | 1-naphthyl |

EXAMPLE 14
(S)- And (R)-Bucindolol Enantiomers

A respective diastereomer of the urea derivative from Example 1 was heated at reflux for 0.5 hr in absolute ethanol with 5 equivalents of 99% hydrazine hydrate. After evaporation of the solvent at reduced pressure, the residue was dissolved in acetonitrile and 5 equivalents of pyruvic acid were added. The solution was stirred at 25° C. overnight and then concentrated at reduced pressure to give a residue that was dissolved in EtOAc. The EtOAc solution was washed with 3 portions each of 1N NaOH and H$_2$O, dried (anhydrous MgSO$_4$), filtered, and concentrated. One equivalent of cyclohexanesulfamic acid was added to a solution of the weighed residue in absolute ethanol. After the mixture had cooled the precipitated salt was collected by filtration. Recrystallization from ethanol-isopropyl ether (Darco G-60) gave analytically pure samples of each isomer.

(S)-(−)-isomer, m.p. 180°-181° C., $[\alpha]_D^{25}$ −15.0° (C 1, CH$_3$OH).

Anal. Calcd. for C$_{22}$H$_{25}$N$_3$O$_2$.C$_6$H$_{13}$NO$_3$S: C, 61.98; H, 7.06; N, 10.33. Found: C, 62.12; H, 7.08; N, 10.31.

NMR (DMSO-d$_6$): 1.16 (4,m), 1.29 (6,s); 1.60 (4,m); 1.99 (2,m); 3.16 (5,m); 4.29 (3,m); 7.20 (6,m); 7.68 (3,m); 8.20 (4,bs); 11.12 (1,bs).

Ir (KBr): 745, 1040, 1210, 1250, 1450, 1495, 1600, 2230, 2860, 2930, 3050, 3300, and 3400 cm$^{-1}$.

(R)-(+)-isomer, m.p. 179°-180° C. $[\alpha]_D^{25}$ +15.5° (C 1, CH$_3$OH).

Anal. Calcd. for C$_{22}$H$_{25}$N$_3$O$_2$.C$_6$H$_{13}$NO$_3$S: C, 61.98; H, 7.06; N, 10.33. Found: C, 62.07; H, 7.14; H, 10.11.

NMR (DMSO-d$_6$): 1.14 (4,m); 1.28 (6,s); 1.60 (4,m); 1.94 (2,m); 3.70 (5,m); 4.25 (3,m); 7.20 (6,m); 7.68 (3,m); 8.00 (4,bs); 11.00 (1,bs).

IR (KBr): 745, 1035, 1215, 1245, 1450, 1495, 1600, 2220, 2860, 2940, 3050, 3210, and 3300 cm$^{-1}$.

Starting with appropriately derived urea diastereomers, other examples of Formula I adrenergic propanolamines may be resolved using substantially the same procedures as outlined hereinabove. Some additional Formula I propanolamines which may be resolved are shown in Table 2.

TABLE 2
Adrenergic Propanolamines $$\text{Z}-\text{O}-\text{CH}_2-\overset{\overset{*}{|}}{\underset{\underset{\text{OX}}{|}}{\text{C}}}-\text{CH}_2-\text{NHY}$$

| Example | X | Y | Z |
|---|---|---|---|
| 15 | H | i-Pr | 2-(2-propenyl)phenyl |
| 16 | H | i-Pr | 1-naphthyl |

TABLE 2-continued

Adrenergic Propanolamines $$Z-O-CH_2-\overset{*}{\underset{OX}{C}}-CH_2-NHY$$

| Example | X | Y | Z |
|---|---|---|---|
| 17 | H | t-Bu | 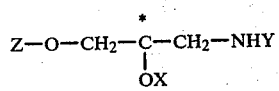 |
| 18 | H | i-Pr | 2-(2-propenyloxy)phenyl |
| 19 | H | i-Pr | (4-1H—indolyl) |
| 20 | H | i-Pr | 4-acetanilide |
| 21 | H | i-Pr | 2-methylthiopenyl |
| 22 | H | i-Pr | 2-cyanopyridyl |
| 23 | H | t-Bu | 2-cyanopyridyl |
| 24 | acetyl | 2-(benzothiophen-3-yl)-1,1-dimethylethyl | 2-cyanophenyl |
| 25 | H | 2-(indol-3-yl)-1,1-dimethylethyl | |
| 26 | H | i-Pr | 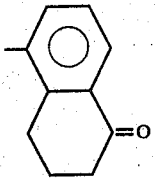 |
| 27 | H | i-Pr | 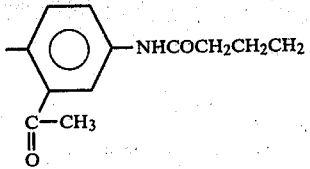 |
| 28 | H | | 3-methylphenyl |
| | | 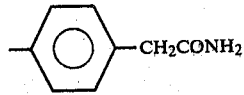 | |
| 29 | H | t-Bu | 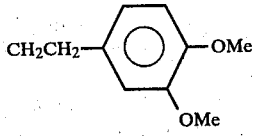 |
| 30 | H | t-Bu | 2-cyanophenyl |
| 31 | H | t-Bu | 2-cyclohexylphenyl |
| 32 | H | i-Pr | 4-indanyl |
| 33 | H | i-Pr | 4- (or 7-) indenyl |
| 34 | H | i-Pr | 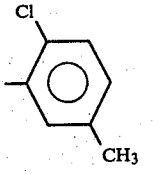 |
| 35 | H | i-Pr | 2-methoxyphenyl |
| 36 | H | i-Pr | 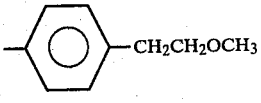 |
| 37 | H | t-Bu | 2-cyclopentylphenyl |

TABLE 2-continued

Adrenergic Propanolamines $$Z-O-CH_2-\overset{*}{\underset{OX}{C}}-CH_2-NHY$$

| Example | X | Y | Z |
|---|---|---|---|
| 38 | H | t-Bu | 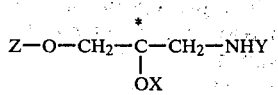 |
| 39 | H | i-Pr | 2-cyclopropylphenyl |
| 40 | H | 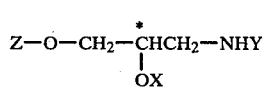 | 2-methylphenyl |
| 41 | H | i-Pr | 3-methylphenyl |
| 42 | H | t-Bu |  |
| 43 | H | t-Bu | 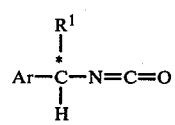 |

What is claimed is:

1. A process for resolving a racemic modification of β-adrenergic aryl- or hetaryl-oxypropanolamines of Formula I $$Z-O-CH_2-\overset{*}{\underset{OX}{C}HCH_2}-NHY \quad (I)$$

wherein
Z is substituted or unsubstituted aryl group such as phenyl, tetralyl, indanyl, indenyl, and naphthyl; or a substituted or unsubstituted hetaryl group such as pyridine, benzopyridine, pyrrole, benzopyrrole, and thiadiazole; with the substituent or substituents bonded to Z being a member or members selected from the group consisting of lower ($C_1$–$C_6$) alkyl, lower alkoxy, lower alkenyl, lower alkenyloxy, lower alkynyl, lower alkynyloxy, lower alkylthio, lower alkanoyl, hydroxy-lower alkyl, cyano, lower cycloalkyl, lower cycloalkenyl, carbamoyl, lower alkylcarbamoyl, carbamoyl-lower alkyl, lower alkyl carbamoyl-lower alkoxy, lower alkoxy-lower alkyl, N-morpholino, hydroxy, and halogen;

Y is $C_1$ to $C_{10}$ alkyl or AB wherein
A is an alkyl chain from 1 to 10 carbons, branched and unbranched, and B is selected from the group consisting of Z, as defined hereinabove, furan, benzofuran, thiophene, benzothiophene, pyrrolidine, and piperidine;

X is hydrogen or $$R-\overset{O}{\underset{\|}{C}}-$$

wherein
R is $C_1$–$C_{10}$ alkyl, phenyl, or alkylphenyl;

which comprises
(1) treating an appropriate β-adrenergic aryl- or hetaryloxypropanolamine of Formula I, as defined hereinabove, with a chiral isocyanate of Formula II $$Ar-\overset{R^1}{\underset{H}{\overset{*}{C}}}-N=C=O \quad (II)$$

wherein
Ar is phenyl or naphthyl either unsubstituted or substituted with a member or members of the group defined as substituents bonded to Z; and
$R^1$ is $C_1$–$C_6$ alkyl; thereby yielding a pair of diastereomeric urea derivatives of Formula III

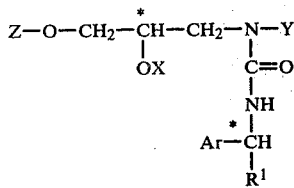 (III)

wherein $R^1$, Ar, X, Y, and Z are as defined hereinabove;

(2) separating the diastereomeric pair of ureas into the individual diastereomers; and (3) generating the propanolamine enantiomer by treating the respective urea diastereomer with an excess of hydrazine hydrate followed by a similar excess of an α-keto carboxylic acid.

2. The process of claim 1 wherein Z is an ortho substituted phenyl ring.

3. The process of claim 1 wherein Z is an ortho substituted pyridine ring.

4. The process of claim 1 wherein A is a $C_2$–$C_4$ alkyl chain, branched and unbranched and B is an indole ring system.

5. The process of claim 1 wherein X is hydrogen.

6. The process of claim 1 wherein $R^1$ is methyl; and Ar is 1-naphthyl.

7. The process of claim 1 wherein the α-keto carboxylic acid used in step (3) is pyruvic acid.

8. The process of claim 1 wherein about 5 equivalents of hydrazine and about 5 equivalents of pyruvic acid per equivalent of intermediate urea III are employed.

9. The process of claim 1 wherein the Formula I compound is chosen from the group consisting of
acebutolol,
alprenolol,
atenolol,
bevantolol,
buprenolol,
bunitrolol,
bunolol,
exaprolol,
indanolol,
metoprolol,
moprolol,
oxprenolol,
pamatolol,
penbutolol,
pargolol,
procinolol,
practolol,
tiprenolol,
tolamolol,
toliprolol,
nadolol,
pindolol, and
timolol.

10. The process of claim 1 wherein the Formula I compound is 2-[2-hydroxy-3-[[2-(1H-indol-3-yl)-1,1-dimethylethyl]amino]propoxy]benzonitrile and the chiral isocyanate is (R)-(−)-1-(1-naphthyl)ethyl isocyanate.

* * * * *